US00PP18182P2

(12) United States Plant Patent
Kanaya

(10) Patent No.: US PP18,182 P2
(45) Date of Patent: Nov. 6, 2007

(54) ***CALIBRACHOA* PLANT NAMED 'SUNBELSAFU'**

(50) Latin Name: ***Calibrachoa* sp.**
Varietal Denomination: Sunbelsafu

(75) Inventor: Takeshi Kanaya, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 11/444,220

(22) Filed: May 31, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—June Hwu
(74) *Attorney, Agent, or Firm*—Jondle & Associates, P.C.

(57) ABSTRACT

A new *calibrachoa* plant particularly distinguished by deep-violet flowers, abundant branching with a great profusion of blooms, continuously flowers from spring to late fall, excellent tolerance to rain and high temperatures, and a vigorous, mounding plant habit is disclosed.

2 Drawing Sheets

Genus and species: *Calibrachoa* sp.
Variety denomination: 'Sunbelsafu'.

BACKGROUND OF THE NEW PLANT

The present invention comprises a new and distinct cultivar of *calibrachoa,* botanically known as *Calibrachoa* sp., and hereinafter referred to by the cultivar name 'Sunbelsafu'. The new cultivar originated from a hybridization made in April 2002 in Higashiomi, Shiga, Japan. The female parent was the proprietary *calibrachoa* plant 'V14' (unpatented), while the male parent was the proprietary *calibrachoa* plant 'P30' (unpatented).

The new cultivar was created in 2002 in Higashiomi, Shiga, Japan and has been asexually reproduced repeatedly by vegetative cuttings in Higashiomi, Shiga, Japan. The present invention has been found to retain its distinctive characteristics through successive asexual propagations.

SUMMARY OF THE INVENTION

The following are the most outstanding and distinguishing characteristics of this new cultivar when grown under normal horticultural practices in Higashiomi, Shiga, Japan.

1. Deep-violet flowers;
2. Abundant branching with a great profusion of blooms;
3. Vigorous and mounding plant habit;
4. Continuously flowers from spring to late fall; and
5. Excellent tolerance to rain and high temperatures.

DESCRIPTION OF PHOTOGRAPHS

This new *calibrachoa* plant is illustrated by the accompanying photographs which show the overall plant habit including blooms, buds and foliage of the plant; the colors shown are as true as can be reasonably obtained by conventional photographic procedures. The photographs are of a 4-month-old plant grown outdoors in Higashiomi, Shiga, Japan.

DESCRIPTION OF THE NEW CULTIVAR

Figure 1:
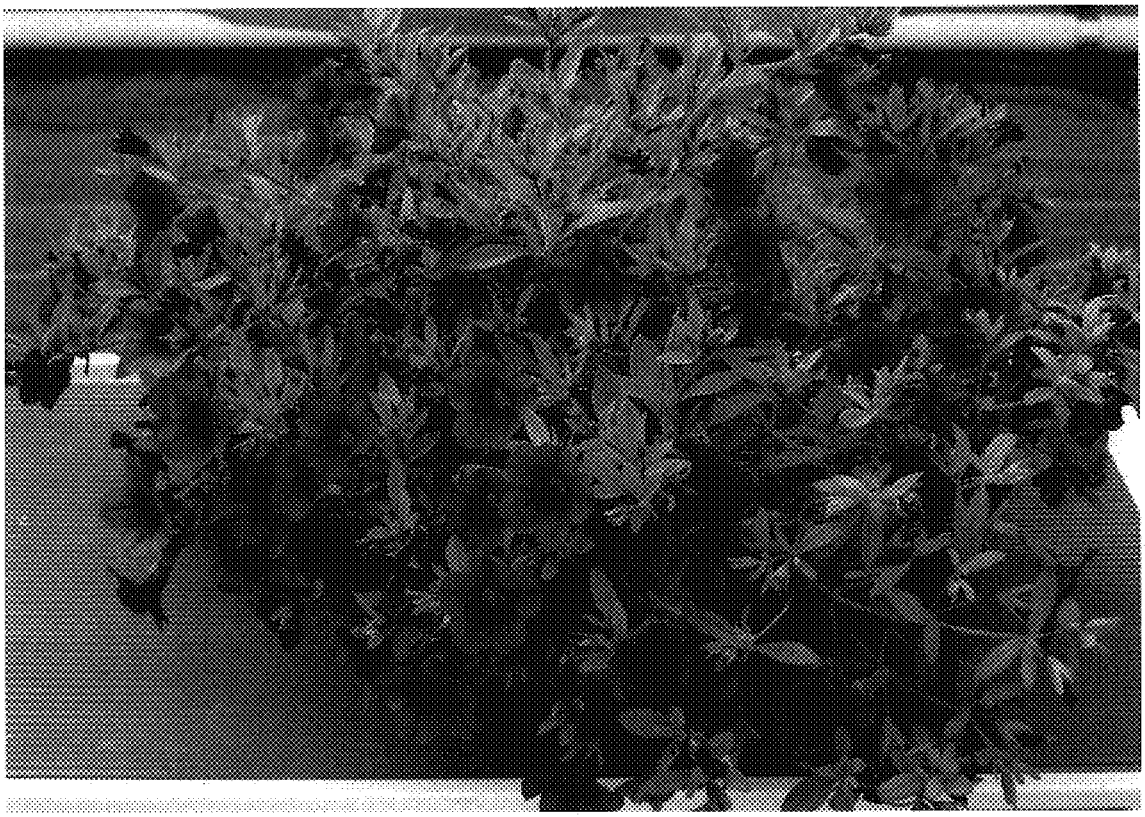
FIG. 1 shows the overall plant habit, including blooms, buds and foliage.
Figure 2:
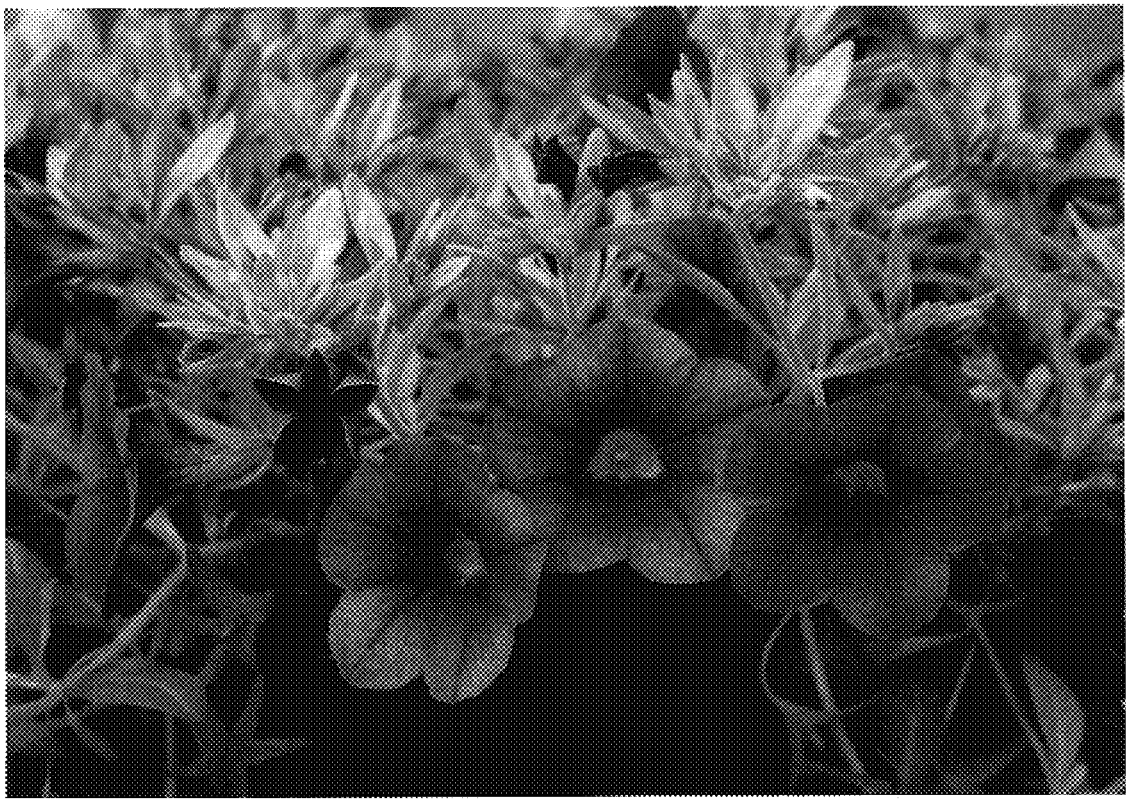
FIG. 2 shows mature flowers.

The following detailed description sets forth the distinctive characteristics of 'Sunbelsafu'. The data which define these characteristics were collected from asexual reproductions carried out in Higashiomi, Shiga, Japan. The plant history was taken on 4-month old plants which were planted as rooted cuttings in 15-cm pots in a spring trial setting in 2005 and grown outdoors in temperatures ranging between 13° C. and 23° C. The plants were pinched once in April 2005. Observations were made when the plants were in full flower in May 2005. Color readings were taken under natural light in the greenhouse. Color references are primarily to The R.H.S. Colour Chart of The Royal Horticultural Society of London (R.H.S.) (2001).

DETAILED BOTANICAL DESCRIPTION

Classification:
- *Family.*—Solanaceae.
- *Botanically.*—*Calibrachoa* sp.
- *Common name.*—*Calibrachoa.*

Parentage:
- *Female parent.*—'V14', a proprietary violet (RHS N87A) flowered *calibrachoa* plant (unpatented).
- *Male parent.*—'P30', a proprietary purple (RHS 75A) flowered *calibrachoa* plant (unpatented).

Growth:
- *Form.*—Annual.
- *Habit.*—Mounding, freely branching and vigorous.
- *Height* (*measured from the top of the soil*).—14.2 cm.
- *Diameter.*—47.2 cm.
- *Propagation.*—Terminal tips for cutting.
- *Time to produce a finished flowering plant.*—About 2 to 3 weeks for a 15-cm pot.
- *Keeping quality.*—210 days.
- *Outdoor plant performance.*—Use in pots, hanging baskets or planters and for use as ground cover; excellent tolerance to rain and high temperatures.
- *Time to initiate and develop roots.*—7 days at 20° C. to 25° C.

*Time to produce rooted cutting or liner* (*young plant*).—21 days at 20° C. to 25° C.

*Root description.*—Light brown, fibrous, fine, fleshy and free-branching.

Stems:

*Description.*—Round in cross-section.

*Number of branches.*—6 basal branches; 40 lateral branches.

*Length of lateral branches.*—17.2 cm.

*Diameter of lateral branches.*—0.17 cm.

*Aspect.*—Upright to outward.

*Stem color.*—RHS 144B.

*Internode length.*—2.5 cm.

*Anthocyanin.*—Absent.

*Texture.*—Pubescent.

Leaves:

*Arrangement.*—Alternate, single leaves, 15 leaves per lateral branch.

*Apex.*—Acute.

*Base.*—Cuneate.

*Margin.*—Entire.

*Color* (*immature leaves*).—Upper surface: RHS 143B. Lower surface: RHS 146C.

*Color* (*mature leaves*).—Upper surface: RHS 147A. Lower surface: RHS 147B.

*Size.*—Length: 3.9 cm. Width: 1.2 cm.

*Shape.*—Narrowly elliptic.

*Texture.*—Pubescent on both upper and lower surfaces.

*Venation.*—Type: Reticulate. Color (both upper and lower surfaces): RHS 144C.

*Petiole.*—Length: 0.9 cm. Diameter: 0.5 cm. Color: RHS 144C. Texture: Pubescent.

Flower buds:

*Color.*—RHS 83A.

*Shape.*—Cylindrical.

*Size.*—Length: 2.3 cm. Diameter: 0.58 cm.

Inflorescence:

*Blooming habit.*—Continuous from spring to late fall.

*Inflorescence type.*—Indefinite, solitary flower, self-cleaning.

*Arrangement.*—Borne in upper leaf axils.

*Aspect.*—Upright to outward.

*Shape.*—Salverform.

*Fragrance.*—None.

*Flower number* (*per inflorescence*).—One.

*Quantity of flowers and buds per plant.*—300.

*Flower longevity on the plant.*—7 to 10 days.

*Peduncle.*—Color: RHS 144B with RHS N199B anthocyanin pigmentation. Length: 2.0 cm. Diameter: 0.6 cm. Texture: Pubescent.

Flowers:

*Size.*—Height (flower depth): 2.7 cm. Diameter: 3.8 cm.

*Corolla tube.*—Shape: Tube-shaped. Tube length: 1.7 cm. Diameter (proximal end): 0.22 cm. Diameter (distal end): 0.84 cm. Color outside: RHS N77B with RHS N77A venation. Color inside: RHS 7B with RHS N79A venation.

*Petals.*—Arrangement: Composed of 5 fused petals arranged in a single whorl. Shape: Spatulate, fused. Size: Length: 1.6 cm. Width: 1.6 cm. Apex: Rounded. Base: Fused. Margin: Entire. Color (when opening): Upper surface: RHS N81A with RHS 83A venation. Lower surface: RHS N78C with RHS N92A venation. Color (fully opened): Upper surface: RHS N81A with RHS 83A venation. Lower surface: RHS N80A with RHS N92A venation. Petal texture (both upper and lower surfaces): Smooth, satiny.

*Calyx.*—Form: Tubular, star-shaped. Length: 1.7 cm. Diameter: 1.8 cm.

*Sepals.*—Arrangement: Single whorl. Number: 5. Shape: Lanceolate. Apex: Acute. Base: Fused. Margin: Entire. Size: Length: 1.7 cm. Width: 0.39 cm. Color (immature): Upper surface: RHS 146B. Lower surface: RHS 200C. Color (mature): Upper surface: RHS 137B. Lower surface: RHS 137C.

Reproductive organs:

*Stamens.*—Quantity: 5. Filament: Length: 0.5 cm to 1.0 cm. Color: RHS 150D. Anther: Shape: Ellipsoid. Size: 0.10 cm. Color: RHS 4C.

*Pollen.*—Amount: Moderate. Color: RHS 8C.

*Pistil.*—Quantity: One. Length: 0.52 cm.

*Style.*—Length: 0.52 cm. Color: RHS 144C.

*Stigma.*—Shape: Transversely ellipsoid. Color: RHS 144C.

*Ovary color.*—RHS 145A.

Fruit and seed set: Seed production has not been observed.

Disease and insect resistance: No particular resistance or susceptibility to diseases or insects noted to date.

COMPARISON WITH PARENTAL AND COMMERCIAL CULTIVARS

'Sunbelsafu' differs from the female parent 'V14' (unpatented), by having deep violet flowers and a mounding growth habit, while 'V14' has violet flowers and a spreading growth habit.

'Sunbelsafu' differs from the male parent 'P30' (unpatented), by having deep violet flowers and shallow corolla lobing, while 'P30' has purple flowers and deeper corolla lobing. Additionally, 'Sunbelsafu' has a larger flower diameter than 'P30'.

'Sunbelsafu' is similar to the commercial variety 'Sunbelchipi' (U.S. Plant Pat. No. 10,355) however, there are differences as listed in Table 1 below:

TABLE 1

Comparison of Characteristics between 'Sunbelsafu' and 'Sunbelchipi'

| Characteristic | 'Sunbelsafu' | 'Sunbelchlpi' |
|---|---|---|
| Stem color | RHS 144B | RHS 144B with RHS N186C anthocyanin |
| Leaf color (immature) | Upper surface: RHS 143B<br>Lower surface: RHS 146C | Upper surface: RHS 137B<br>Lower surface: RHS 137C |
| Leaf color (mature) | Upper surface: RHS 147A<br>Lower surface: RHS 147B | Upper surface: RHS 137B<br>Lower surface: RHS 137C |
| Petiole length | 0.9 cm | 0.32 cm |
| Flower bud color | RHS 83A | RHS 59C |
| Flower diameter | 3.8 cm | 3.3 cm |
| Petal apex | Rounded | Truncate |
| Petal color (when opening) | Upper surface: RHS N81A with RHS 83A venation<br>Lower surface: RHS 78C with RHS N92A venation | Upper surface: RHS N57A<br>Lower surface: RHS 66B with RHS N186C venation |
| Petal color (fully opened) | Upper surface: RHS N81A with RHS 83A venation<br>Lower surface: RHS N80A with RHS N92A venation | Upper surface: RHS N66A<br>Lower surface: RHS N66C |
| Corolla tube diameter (distal end) | 0.84 cm | 0.77 cm |

TABLE 1-continued

Comparison of Characteristics between 'Sunbelsafu' and 'Sunbelchipi'

| Characteristic | 'Sunbelsafu' | 'Sunbelchlpi' |
|---|---|---|
| Corolla tube color (inside) | RHS 7B with RHS N79A venation | RHS 9A with RHS N186C venation |
| Corolla tube color (outside) | RHS N77B with RHS N77A venation | RHS 150D with RHS N186C venation |
| Sepal apex | Acute | Obtuse |
| Sepal width | 0.39 cm | 0.26 cm |
| Sepal color (immature) | Upper surface: RHS 146B<br>Lower surface: RHS 200C | Upper surface: RHS 137B<br>Lower surface: RHS 137C |

TABLE 1-continued

Comparison of Characteristics between 'Sunbelsafu' and 'Sunbelchipi'

| Characteristic | 'Sunbelsafu' | 'Sunbelchlpi' |
|---|---|---|
| Peduncle color | RHS 144B | RHS 143B |
| Anther color | RHS 4C | RHS 16C |

I claim:

1. A new and distinct cultivar of *calibrachoa* plant as shown and described herein.

* * * * *